United States Patent [19]
Lin et al.

[11] Patent Number: 5,847,099
[45] Date of Patent: Dec. 8, 1998

[54] TNF RECEPTOR DEATH DOMAIN LIGAND PROTEINS

[75] Inventors: Lih-Ling Lin, Concord; Jennifer Chen, Chestnut Hill, both of Mass.

[73] Assignee: Genetics Institute, Inc., Cambridge, Mass.

[21] Appl. No.: 649,341

[22] Filed: May 17, 1996

Related U.S. Application Data

[63] Continuation of Ser. No. 327,514, Oct. 19, 1994, abandoned.

[51] Int. Cl.$^6$ .............................. C12N 15/12; C12N 5/10; C12N 15/63; C07K 14/47
[52] U.S. Cl. ...................... 536/23.5; 435/69.1; 435/325; 435/252.3; 435/254.11; 435/320.1; 530/350
[58] Field of Search .................................. 435/69.1, 325, 435/252.3, 254.11, 320.1; 536/23.5; 530/350, 351

[56] References Cited

U.S. PATENT DOCUMENTS

| | | | |
|---|---|---|---|
| 5,296,592 | 3/1994 | Dower et al. | 530/413 |
| 5,464,938 | 11/1995 | Smith et al. | 530/350 |
| 5,506,340 | 4/1996 | Heavner | 530/324 |
| 5,563,039 | 10/1996 | Goeddel et al. | 435/7.1 |

FOREIGN PATENT DOCUMENTS

| | | |
|---|---|---|
| A-46127/93 | 9/1993 | Australia . |
| 308378 | 3/1989 | European Pat. Off. . |
| 393438 | 4/1990 | European Pat. Off. . |
| 433900 | 6/1991 | European Pat. Off. . |
| 526905 | 2/1993 | European Pat. Off. . |
| 585 939 | 3/1993 | European Pat. Off. . |
| WO 92/03470 | 3/1992 | WIPO . |
| WO 92/03471 | 3/1992 | WIPO . |
| WO 92/14834 | 9/1992 | WIPO . |
| WO 93/19777 | 10/1993 | WIPO . |
| WO 94/01548 | 1/1994 | WIPO . |
| WO 94/10207 | 5/1994 | WIPO . |
| WO 95/31544 | 11/1995 | WIPO . |
| WO 95/33051 | 12/1995 | WIPO . |
| 96/25941 | 8/1996 | WIPO . |

OTHER PUBLICATIONS

Waye et al., Protein Engineering 8:90 (1995).
Auffray et al., Life Sciences 318:263–272 (1995).
Rothe et al., Cell 78:681–692 (1994).
Song et al., The Journal of Biological Chemistry 269:22492–22495 (1994).
Boldin et al., The Journal of Biological Chemistry 270(1):387–391 (1995).
Hsu et al., Cell 81:495–504 (1995).
Boldin et al., FEBS Letters 367:39–44 (1995).
Schall et al., Cell 61:361–370 (1990).
Tartaglia et al., Cell 74:845–853 (1993).
Shimasaki et al., J. Biol. Chem. 266:10646–10653 (1991).
Saragovi et al., Bio/Technology 10:773–778 (1992).
McDowell et al., J. Amer. Chem. Soc. 114:9245–9253 (1992).
Kaufman et al., Nucleic Acids Res. 19:4485–4490 (1991).
Kaufman et al., Methods in Enzymology 185:537–566 (1990).
Gyuris et al., Cell 75:791–803 (1993).
Gietz et al., Nucleic Acids Res. 20:1425 (1992).
Luban and Goff, 1995, Curr. Opin. Biotech. 6:59–64.
Tartaglia et al., 1992, J. Biol. Chem. 267(7):4304–4307.
Tartaglia et al., 1993, Cell 73:213–216.
GenBank Accession No. U44953; 01 Jul. 1996.
GenBank Accession No. U48254; 03 Aug. 1996.
Miki et al. (1992) Cancer Res. 52: 643.
Darnay et al. (1994) J. Biol. Chem. 269:20299.
Kiefer et al. (1992) J. Biol. Chem. 267: 12692.
Genbank accession No. T08593 (1993).
Genbank accession No. T07800 (1993).
Genbank accession No. M78050 (1992).
Genbank accession No. M78539 (1992).

*Primary Examiner*—Stephen Walsh
*Assistant Examiner*—Claire M. Kaufman
*Attorney, Agent, or Firm*—Scott A. Brown; Thomas J. DesRosier

[57] ABSTRACT

Novel TNF receptor death domain ("TNF-R1-DD") ligand proteins are disclosed. Polynucleotides encoding the TNF-R1-DD ligand protein are also disclosed, along with vectors, host cells, and methods of making the TNF-R1-DD ligand protein. Pharmaceutical compositions containing the TNF-R1-DD ligand protein, methods of treating inflammatory conditions, and methods of inhibiting TNF-R death domain binding are also disclosed. Methods of identifying inhibitors of TNF-R death domain binding and inhibitors identified by such methods are also disclosed.

15 Claims, 2 Drawing Sheets

Fig. 2

TNF RECEPTOR DEATH DOMAIN LIGAND PROTEINS

This application is a continuation of application Ser. No. 08/327,514, filed Oct. 19, 1994, now abandoned.

BACKGROUND OF THE INVENTION

The present invention relates to the field of anti-inflammatory substances and other substances which act by inhibiting binding to the intracellular domain of a tumor necrosis factor receptor (hereinafter "TNF-R"), such as, for example, the P55 type (or TNF-R1) TNF receptor. More particularly, the present invention is directed to novel ligands which bind to the TNF-R intracellular domain and to inhibition or modulation of signal transduction by this receptor.

Tumor necrosis factor (herein "TNF") is a cytokine which produces a wide range of cellular activities. TNF causes an inflammatory response, which can be beneficial, such as in mounting an immune response to a pathogen, or when overexpressed can lead to other detrimental effects of inflammation.

The cellular effects of TNF are initiated by the binding of TNF to its receptors (TNF-Rs) on the surface of target cells. The isolation of polynucleotides encoding TNF-Rs and variant forms of such receptors has been described in European patent publication Nos. EP 308,378, EP 393,438, EP 433,900, EP 526,905 and EP 568,925; in PCT patent publication Nos. WO91/03553 and WO93/19777; and by Schall et al., Cell 61:361–370 (1990) (disclosing the P55 type TNF receptor). Processes for purification of TNF-Rs have also been disclosed in U.S. Pat. No. 5,296,592.

Native TNF-Rs are characterized by distinct extracellular, transmembrane and intracellular domains. The primary purpose of the extracellular domain is to present a binding site for TNF on the outside of the cell. When TNF is bound to the binding site, a "signal" is transmitted to the inside of the cell through the transmembrane and intracellular domains, indicating that binding has occurred. Transmission or "transduction" of the signal to the inside of the cell occurs by a change in conformation of the transmembrane and/or intracellular domains of the receptor. This signal is "received" by the binding of proteins and other molecules to the intracellular domain of the receptor, resulting in the effects seen upon TNF stimulation. Two distinct TNF receptors of ~55 kd ("TNF-R1") and ~75 kd ("TNF-R2") have been identified. Numerous studies with anti-TNF receptor antibodies have demonstrated that TNF-R1 is the receptor which signals the majority of the pleiotropic activities of TNF. Recently, the domain required for signaling cytotoxicity and other TNF-mediated responses has been mapped to the ~80 amino acid near the C-terminus of TNF-R1. This domain is therefore termed the "death domain" (hereinafter referred to as "TNF-R death domain" and "TNF-R1-DD") (see, Tartaglia et al., Cell 74:845–853 (1993)).

While TNF binding by TNF-Rs results in beneficial cellular effects, it is often desirable to prevent or deter TNF binding from causing other detrimental cellular effects. Although substantial effort has been expended investigating inhibition of TNF binding to the extracellular domain of TNF-Rs, examination of binding of proteins and other molecules to the intracellular domain of TNF-Rs has received much less attention.

However, ligands which bind to the TNF-R intracellular domain have yet to be identified. It would be desirable to identify and isolate such ligands to examine their effects upon TNF-R signal transduction and their use as therapeutic agents for treatment of TNF-induced conditions. Furthermore, identification of such ligands would provide a means for screening for inhibitors of TNF-R/intracellular ligand binding, which will also be useful as anti-inflammatory agents.

SUMMARY OF THE INVENTION

Applicants have for the first time identified novel TNF-R1-DD ligand proteins and have isolated polynucleotides encoding such ligands. Applicants have also identified a known protein which may also bind to the death domain of TNF-R.

In one embodiment, the present invention provides a composition comprising an isolated polynucleotide encoding a protein having TNF-R1-DD ligand protein activity. In preferred embodiments, the polynucleotide is selected from the group consisting of:

(a) a polynucleotide comprising the nucleotide sequence of SEQ ID NO:1 from nucleotide 2 to nucleotide 1231;

(b) a polynucleotide comprising a fragment of the nucleotide sequence of SEQ ID NO:1;

(c) a polynucleotide encoding an TNF-R1-DD ligand protein comprising the amino acid sequence of SEQ ID NO:2;

(d) a polynucleotide encoding an TNF-R1-DD ligand protein comprising a fragment of the amino acid sequence of SEQ ID NO:2;

(e) a polynucleotide comprising the nucleotide sequence of SEQ ID NO:3 from nucleotide 2 to nucleotide 415;

(f) a polynucleotide comprising a fragment of the nucleotide sequence of SEQ ID NO:3;

(g) a polynucleotide encoding an TNF-R1-DD ligand protein comprising the amino acid sequence of SEQ ID NO:4;

(h) a polynucleotide encoding an TNF-R1-DD ligand protein comprising a fragment of the amino acid sequence of SEQ ID NO:4; and (i) a polynucleotide capable of hybridizing under stringent conditions to any one of the polynucleotides specified in (a)–(h). In certain preferred embodiments, the polynucleotide is operably linked to an expression control sequence. The invention also provides a host cell, including bacterial, yeast, insect and mammalian cells, transformed with such polynucleotide compositions.

Processes are also provided for producing an TNF-R1-DD ligand protein, which comprises:

(a) growing a culture of the host cell transformed with such polynucleotide compositions in a suitable culture medium; and (b) purifying the TNF-R1-DD ligand protein from the culture. The ligand protein produced according to such methods is also provided by the present invention.

Compositions comprising a protein having TNF-R1-DD ligand protein activity are also disclosed. In preferred embodiments the protein comprises an amino acid sequence selected from the group consisting of:

(a) the amino acid sequence of SEQ ID NO:2;

(b) fragments of the amino acid sequence of SEQ ID NO:2;

(c) the amino acid sequence of SEQ ID NO:4;

(d) fragments of the amino acid sequence of SEQ ID NO:4;

(e) the amino acid sequence of SEQ ID NO:6;

(f) fragments of the amino acid sequence of SEQ ID NO:6; the protein being substantially free from other mammalian proteins. Such compositions may further comprise a pharmaceutically acceptable carrier.

Compositions comprising an antibody which specifically reacts with such TNF-R1-DD ligand protein are also provided by the present invention.

Methods are also provided for identifying an inhibitor of TNF-R death domain binding which comprise:

(a) combining an TNF-R death domain protein with an TNF-R1-DD ligand protein, said combination forming a first binding mixture;

(b) measuring the amount of binding between the TNF-R death domain protein and the TNF-R1-DD ligand protein in the first binding mixture;

(c) combining a compound with the TNF-R death domain protein and an TNF-R1-DD ligand protein to form a second binding mixture;

(d) measuring the amount of binding in the second binding mixture; and (e) comparing the amount of binding in the first binding mixture with the amount of binding in the second binding mixture;

wherein the compound is capable of inhibiting TNF-R death domain binding when a decrease in the amount of binding of the second binding mixture occurs. In certain preferred embodiments the TNF-R1-DD ligand protein used in such method comprises an amino acid sequence selected from the group consisting of:

(a) the amino acid sequence of SEQ ID NO:2;
(b) fragments of the amino acid sequence of SEQ ID NO:2;
(c) the amino acid sequence of SEQ ID NO:4;
(d) fragments of the amino acid sequence of SEQ ID NO:4;
(e) the amino acid sequence of SEQ ID NO:6;
(f) fragments of the amino acid sequence of SEQ ID NO:6;
(g) the amino acid sequence of SEQ ID NO:8; and
(h) fragments of the amino acid sequence of SEQ ID NO:8.

Compositions comprising inhibitors identified according to such method are also provided. Such compositions may include pharmaceutically acceptable carriers.

Methods are also provided for preventing or ameliorating an inflammatory condition which comprises administering a therapeutically effective amount of a composition comprising a protein having TNF-R1-DD ligand protein activity and a pharmaceutically acceptable carrier.

Other embodiments provide methods of inhibiting TNF-R death domain binding comprising administering a therapeutically effective amount of a composition comprising a protein having TNF-R1-DD ligand protein activity and a pharmaceutically acceptable carrier.

Methods are also provided for preventing or ameliorating an inflammatory condition which comprises administering to a mammalian subject a therapeutically effective amount of a composition comprising a pharmaceutically acceptable carrier and a protein selected from the group consisting of insulin-like growth factor binding protein-5 ("IGFBP-5"), and fragments thereof having TNF-R1-DD ligand protein activity. Such proteins may also be administered for inhibiting TNF-R death domain binding.

Methods of preventing or ameliorating an inflammatory condition or of inhibiting TNF-R death domain binding are provided, which comprise administering to a mammalian subject a therapeutically effective amount of inhibitors of TNF-R death domain binding, are also provided.

Methods of identifying an inhibitor of TNF-R death domain binding are also provided by the present invention which comprise:

(a) transforming a cell with a first polynucleotide encoding an TNF-R death domain protein, a second polynucleotide encoding an TNF-R1-DD ligand protein, and at least one reporter gene, wherein the expression of the reporter gene is regulated by the binding of the TNF-R1-DD ligand protein encoded by the second polynucleotide to the TNF-R death domain protein encoded by the first polynucleotide;

(b) growing the cell in the presence of and in the absence of a compound; and (c) comparing the degree of expression of the reporter gene in the presence of and in the absence of the compound;

wherein the compound is capable of inhibiting TNF-R death domain binding when a decrease in the degree of expression of the reporter gene occurs. In preferred embodiments, the cell is a yeast cell and the second polynucleotide is selected from the group consisting of:

(a) a polynucleotide comprising the nucleotide sequence of SEQ ID NO:1 from nucleotide 2 to nucleotide 1231;
(b) a polynucleotide comprising a fragment of the nucleotide sequence of SEQ ID NO:1, which encodes a protein having TNF-R1-DD ligand protein activity;
(c) a polynucleotide encoding an TNF-R1-DD ligand protein comprising the amino acid sequence of SEQ ID NO:2;
(d) a polynucleotide encoding an TNF-R1-DD ligand protein comprising a fragment of the amino acid sequence of SEQ ID NO:2 and having TNF-R1-DD ligand protein activity;
(e) a polynucleotide comprising the nucleotide sequence of SEQ ID NO:3 from nucleotide 2 to nucleotide 415;
(f) a polynucleotide comprising a fragment of the nucleotide sequence of SEQ ID NO:3, which encodes a protein having TNF-R1-DD ligand protein activity;
(g) a polynucleotide encoding an TNF-R1-DD ligand protein comprising the amino acid sequence of SEQ ID NO:4;
(h) a polynucleotide encoding an TNF-R1-DD ligand protein comprising a fragment of the amino acid sequence of SEQ ID NO:4 and having TNF-R1-DD ligand protein activity;
(i) a polynucleotide comprising the nucleotide sequence of SEQ ID NO:5 from nucleotide 2 to nucleotide 559;
(j) a polynucleotide comprising a fragment of the nucleotide sequence of SEQ ID NO:5, which encodes a protein having TNF-R1-DD ligand protein activity;
(k) a polynucleotide encoding an TNF-R1-DD ligand protein comprising the amino acid sequence of SEQ ID NO:6;
(l) a polynucleotide encoding an TNF-R1-DD ligand protein comprising a fragment of the amino acid sequence of SEQ ID NO:6 and having TNF-R1-DD ligand protein activity;
(m) a polynucleotide comprising the nucleotide sequence of SEQ ID NO:7 from nucleotide 57 to nucleotide 875;

(n) a polynucleotide comprising a fragment of the nucleotide sequence of SEQ ID NO:7, which encodes a protein having TNF-R1-DD ligand protein activity;

(o) a polynucleotide encoding an TNF-R1-DD ligand protein comprising the amino acid sequence of SEQ ID NO:8;

(p) a polynucleotide encoding an TNF-R1-DD ligand protein comprising a fragment of the amino acid sequence of SEQ ID NO:8 and having TNF-R1-DD ligand protein activity; and (q) a polynucleotide capable of hybridizing under stringent conditions to any one of the polynucleotides specified in (a)–(p), which encodes a protein having TNF-R1-DD ligand protein activity.

DETAILED DESCRIPTION OF THE INVENTION

The present inventors have for the first time identified and isolated novel polynucleotides which encode proteins which bind to the TNF-R death domain. As used herein "TNF-R" includes all receptors for tumor necrosis factor. The P55 type TNF-R is the preferred receptor for practicing the present invention.

The sequence of a polynucleotide encoding one such protein is set forth in SEQ ID NO:1 from nucleotides 2 to 1231. This polynucleotide has been identified as "clone 2DD" The amino acid sequence of the TNF-R1-DD ligand protein encoded by clone 2DD is set forth in SEQ ID NO:2. It is believed that clone 2DD is a partial cDNA clone of a longer full length coding sequence. However, as demonstrated herein the protein encoded by clone 2DD does bind the death domain of TNF-R (i.e., has "TNF-R1-DD ligand protein activity" as defined herein). Clone 2DD was deposited with the American Type Culture Collection on Oct. 13, 1994 and given the accession number ATCC 69706.

The protein encoded by clone 2DD is 410 amino acids in length. No identical or closely related sequences were found using BLASTN/BLASTX or FASTA searches. Therefore, clone 2DD encodes a novel protein.

The sequence of a polynucleotide encoding one such protein is set forth in SEQ ID NO:3 from nucleotides 2 to 415. This polynucleotide has been identified as "clone 3DD" The amino acid sequence of the TNF-R1-DD ligand protein encoded by clone 3DD is set forth in SEQ ID NO:4. It is believed that clone 3DD is a partial cDNA clone of a longer full length coding sequence. However, as demonstrated herein the protein encoded by clone 3DD does bind the death domain of TNF-R (i.e., has "TNF-R1-DD ligand protein activity" as defined herein). Clone 3DD was deposited with the American Type Culture Collection on Oct. 13, 1994 and given the accession number ATCC 69705.

The protein encoded by clone 3DD is 138 amino acids. No identical or closely related sequences were found using BLASTN/BLASTX or FASTA searches. Therefore, clone 3DD encodes a novel protein.

The sequence of a polynucleotide encoding another such protein is set forth in SEQ ID NO:5 from nucleotides 2 to 559. This polynucleotide has been identified as "clone 20DD." The amino acid sequence of the TNF-R1-DD ligand protein encoded by clone 20DD is set forth in SEQ ID NO:6. It is believed that clone 20DD is a partial cDNA clone of a longer full length coding sequence. However, as demonstrated herein the protein encoded by clone 20DD does bind the death domain of TNF-R (i.e., has "TNF-R1-DD ligand protein activity" as defined herein). Clone 20DD was deposited with the American Type Culture Collection on Oct. 13, 1994 and given the accession number ATCC 69704.

The protein encoded by clone 20DD is identical to amino acids 87 to 272 of insulin-like growth factor binding protein-5 ("IGFBP-5"), a sequence for which was disclosed in J. Biol. Chem. 266:10646–10653 (1991) by Shimasaki et al., which is incorporated herein by reference. The polynucleotide and amino acid sequences of IGFBP-5 are set forth in SEQ ID NO:7 and SEQ ID NO:8, respectively. Based upon the sequence identity between clone 20DD and IGFBP-5, IGFBP-5 and certain fragments thereof will exhibit TNF-R1-DD ligand binding activity (as defined herein).

For the purposes of the present application, "TNF-R1-DD ligand protein" includes proteins which exhibit TNF-R1-DD ligand protein activity. For the purposes of the present application, a protein is defined as having "TNF-R1-DD ligand protein activity" when it binds to a protein derived from the TNF-R death domain. Activity can be measured by using any assay which will detect binding to an TNF-R death domain protein. Examples of such assays include without limitation the interaction trap assays and assays in which TNF-R death domain protein which is affixed to a surface in a manner conducive to observing binding, including without limitation those described in Examples 1 and 3. As used herein an "TNF-R death domain protein" includes the entire death domain or fragments thereof.

Fragments of the TNF-R1-DD ligand protein which are capable of interacting with the TNF-R death domain or which are capable of inhibiting TNF-R death domain binding (i.e., exhibit TNF-R1-DD ligand protein activity) are also encompassed by the present invention. Fragments of the TNF-R1-DD ligand protein may be in linear form or they may be cyclized using known methods, for example, as described in H. U. Saragovi, et al., Bio/Technology 10, 773–778 (1992) and in R. S. McDowell, et al., J. Amer. Chem. Soc. 114, 9245–9253 (1992), both of which are incorporated herein by reference. Such fragments may be fused to carrier molecules such as immunoglobulins for many purposes, including increasing the valency of TNF-R1-DD ligand protein binding sites. For example, fragments of the TNF-R1-DD ligand protein may be fused through "linker" sequences to the Fc portion of an immunoglobulin. For a bivalent form of the TNF-R1-DD ligand protein, such a fusion could be to the Fc portion of an IgG molecule. Other immunoglobulin isotypes may also be used to generate such fusions. For example, an TNF-R1-DD ligand protein—IgM fusion would generate a decavalent form of the TNF-R1-DD ligand protein of the invention.

The isolated polynucleotide of the invention may be operably linked to an expression control sequence such as the pMT2 or pED expression vectors disclosed in Kaufman et al., Nucleic Acids Res. 19, 4485–4490 (1991), in order to produce the TNF-R1-DD ligand protein recombinantly. Many suitable expression control sequences are known in the art. General methods of expressing recombinant proteins are also known and are exemplified in R. Kaufman, Methods in Enzymology 185, 537–566 (1990). As defined herein "operably linked" means that the isolated polynucleotide of the invention and the expression control sequence are situated within a vector or cell in such a way that the TNF-R1-

DD ligand protein is expressed by a host cell which has been transformed (transfected) with the ligated polynucleotide/expression control sequence.

A number of types of cells may act as suitable host cells for expression of the TNF-R1-DD ligand protein. Host cells include, for example, monkey COS cells, Chinese Hamster Ovary (CHO) cells, human kidney 293 cells, human epidermal A431 cells, human Colo205 cells, 3T3 cells, CV-1 cells, other transformed primate cell lines, normal diploid cells, cell strains derived from in vitro culture of primary tissue, primary explants, HeLa cells, mouse L cells, BHK, HL-60, U937, HaK or Jurkat cells.

The TNF-R1-DD ligand protein may also be produced by operably linking the isolated polynucleotide of the invention to suitable control sequences in one or more insect expression vectors, and employing an insect expression system. Materials and methods for baculovirus/insect cell expression systems are commercially available in kit form from, e.g., Invitrogen, San Diego, Calif., U.S.A. (the MaxBac® kit), and such methods are well known in the art, as described in Summers and Smith, *Texas Agricultural Experiment Station Bulletin No.* 1555 (1987), incorporated herein by reference.

Alternatively, it may be possible to produce the TNF-R1-DD ligand protein in lower eukaryotes such as yeast or in prokaryotes such as bacteria. Potentially suitable yeast strains include *Saccharomyces cerevisiae, Schizosaccharomyces pombe,* Kluyveromyces strains, Candida, or any yeast strain capable of expressing heterologous proteins. Potentially suitable bacterial strains include *Escherichia coli, Bacillus subtilis, Salmonella typhimurium,* or any bacterial strain capable of expressing heterologous proteins. If the TNF-R1-DD ligand protein is made in yeast or bacteria, it may be necessary to modify the protein produced therein, for example by phosphorylation or glycosylation of the appropriate sites, in order to obtain the functional TNF-R1-DD ligand protein. Such covalent attachments may be accomplished using known chemical or enzymatic methods.

The TNF-R1-DD ligand protein of the invention may also be expressed as a product of transgenic animals, e.g., as a component of the milk of transgenic cows, goats, pigs, or sheep which are characterized by somatic or germ cells containing a nucleotide sequence encoding the TNF-R1-DD ligand protein.

The TNF-R1-DD ligand protein of the invention may be prepared by culturing transformed host cells under culture conditions suitable to express the recombinant protein. The resulting expressed protein may then be purified from such culture (i.e., from culture medium or cell extracts) using known purification processes, such as gel filtration and ion exchange chromatography. The purification of the TNF-R1-DD ligand protein may also include an affinity column containing the TNF-R death domain or other TNF-R death domain protein; one or more column steps over such affinity resins as concanavalin A-agarose, heparin-toyopearl® or Cibacrom blue 3GA Sepharose®; one or more steps involving hydrophobic interaction chromatography using such resins as phenyl ether, butyl ether, or propyl ether; or immunoaffinity chromatography.

Alternatively, the TNF-R1-DD ligand protein of the invention may also be expressed in a form which will facilitate purification. For example, it may be expressed as a fusion protein, such as those of maltose binding protein (MBP) or glutathione-S-transferase (GST). Kits for expression and purification of such fusion proteins are commercially available from New England BioLab (Beverly, Mass.) and Pharmacia (Piscataway, N.J.), respectively. The TNF-R ligand protein can also be tagged with an epitope and subsequently purified by using a specific antibody directed to such epitope. One such epitope ("Flag", SEQ ID NO: 9) is commercially available from Kodak (New Haven, Conn.).

Finally, one or more reverse-phase high performance liquid chromatography (RP-HPLC) steps employing hydrophobic RP-HPLC media, e.g., silica gel having pendant methyl or other aliphatic groups, can be employed to further purify the TNF-R1-DD ligand protein. Some or all of the foregoing purification steps, in various combinations, can also be employed to provide a substantially homogeneous isolated recombinant protein. The TNF-R1-DD ligand protein thus purified is substantially free of other mammalian proteins and is defined in accordance with the present invention as an "isolated TNF-R1-DD ligand protein."

TNF-R1-DD ligand proteins may also be produced by known conventional chemical synthesis. Methods for constructing the proteins of the present invention by synthetic means are known to those skilled in the art. The synthetically-constructed protein sequences, by virtue of sharing primary, secondary or tertiary structural and/or conformational characteristics with TNF-R1-DD ligand proteins may possess biological properties in common therewith, including TNF-R1-DD ligand protein activity. Thus, they may be employed as biologically active or immunological substitutes for natural, purified TNF-R1-DD ligand proteins in screening of therapeutic compounds and in immunological processes for the development of antibodies.

The TNF-R1-DD ligand proteins provided herein also include proteins characterized by amino acid sequences similar to those of purified TNF-R1-DD ligand proteins but into which modification are naturally provided or deliberately engineered. For example, modifications in the peptide or DNA sequences can be made by those skilled in the art using known techniques. Modifications of interest in the TNF-R1-DD ligand protein sequences may include the replacement, insertion or deletion of a selected amino acid residue in the coding sequence. For example, one or more of the cysteine residues may be deleted or replaced with another amino acid to alter the conformation of the molecule. Mutagenic techniques for such replacement, insertion or deletion are well known to those skilled in the art (see, e.g., U.S. Pat. No. 4,518,584).

Other fragments and derivatives of the sequences of TNF-R1-DD ligand proteins which would be expected to retain TNF-R1-DD ligand protein activity in whole or in part and may thus be useful for screening or other immunological methodologies may also be easily made by those skilled in the art given the disclosures herein. Such modifications are believed to be encompassed by the present invention.

TNF-R1-DD ligand protein of the invention may also be used to screen for agents which are capable of inhibiting or blocking binding of an TNF-R1-DD ligand protein to the death domain of TNF-R, and thus may act as inhibitors of TNF-R death domain binding and/or TNF activity. Binding assays using a desired binding protein, immobilized or not, are well known in the art and may be used for this purpose using the TNF-R1-DD ligand protein of the invention. Examples 1 and 3 describe examples of such assays. Appropriate screening assays may be cell-based or cell-free. Alternatively, purified protein based screening assays may be used to identify such agents. For example, TNF-R1-DD ligand protein may be immobilized in purified form on a carrier and binding to purified TNF-R death domain may be measured in the presence and in the absence of potential inhibiting agents. A suitable binding assay may alternatively employ purified TNF-R death domain immobilized on a carrier, with a soluble form of a TNF-R1-DD ligand protein of the invention. Any TNF-R1-DD ligand protein may be used in the screening assays described above.

In such a screening assay, a first binding mixture is formed by combining TNF-R death domain protein and TNF-R1-DD ligand protein, and the amount of binding in the first binding mixture ($B_o$) is measured. A second binding mixture is also formed by combining TNF-R death domain protein, TNF-R1-DD ligand protein, and the compound or agent to be screened, and the amount of binding in the second binding mixture (B) is measured. The amounts of binding in the first and second binding mixtures are compared, for example, by performing a $B/B_o$ calculation. A compound or agent is considered to be capable of inhibiting TNF-R death domain binding if a decrease in binding in the second binding mixture as compared to the first binding mixture is observed. The formulation and optimization of binding mixtures is within the level of skill in the art. Such binding mixtures may also contain buffers and salts necessary to enhance or to optimize binding, and additional control assays may be included in the screening assay of the invention.

Alternatively, appropriate screening assays may be cell based. For example, the binding or interaction between an TNF-R ligand protein and the TNF-R death domain can be measured in yeast as described below in Examples 1 and 3.

Compounds found to reduce, preferably by at least about 10%, more preferably greater than about 50% or more, the binding activity of TNF-R1-DD ligand protein to TNF-R death domain may thus be identified and then secondarily screened in other binding assays, including in vivo assays. By these means compounds having inhibitory activity for TNF-R death domain binding which may be suitable as anti-inflammatory agents may be identified.

Isolated TNF-R1-DD ligand protein may be useful in treating, preventing or ameliorating inflammatory conditions and other conditions, such as cachexia, autoimmune disease, graft versus host reaction, osteoporosis, colitis, myelogenous leukemia, diabetes, wasting, and atherosclerosis. Isolated TNF-R1-DD ligand protein may be used itself as an inhibitor of TNF-R death domain binding or to design inhibitors of TNF-R death domain binding. Inhibitors of binding of TNF-R1-DD ligand protein to the TNF-R death domain ("TNF-R intracellular binding inhibitors") are also useful for treating such conditions.

The present invention encompasses both pharmaceutical compositions and therapeutic methods of treatment or use which employ isolated TNF-R1-DD ligand protein and/or binding inhibitors of TNF-R intracellular binding.

Isolated TNF-R1-DD ligand protein or binding inhibitors (from whatever source derived, including without limitation from recombinant and non-recombinant cell lines) may be used in a pharmaceutical composition when combined with a pharmaceutically acceptable carrier. Such a composition may also contain (in addition to TNF-R1-DD ligand protein or binding inhibitor and a carrier) diluents, fillers, salts, buffers, stabilizers, solubilizers, and other materials well known in the art. The term "pharmaceutically acceptable" means a non-toxic material that does not interfere with the effectiveness of the biological activity of the active ingredient(s). The characteristics of the carrier will depend on the route of administration. The pharmaceutical composition of the invention may also contain cytokines, lymphokines, or other hematopoietic factors such as M-CSF, GM-CSF, TNF, IL-2, IL-3, IL-4, IL-5, IL-6, IL-7, IL-8, IL-9, TNF0, TNF1, TNF2, G-CSF, Meg-CSF, stem cell factor, and erythropoietin. The pharmaceutical composition may further contain other anti-inflammatory agents. Such additional factors and/or agents may be included in the pharmaceutical composition to produce a synergistic effect with isolated TNF-R1-DD ligand protein or binding inhibitor, or to minimize side effects caused by the isolated TNF-R1-DD ligand protein or binding inhibitor. Conversely, isolated TNF-R1-DD ligand protein or binding inhibitor may be included in formulations of the particular cytokine, lymphokine, other hematopoietic factor, thrombolytic or anti-thrombotic factor, or anti-inflammatory agent to minimize side effects of the cytokine, lymphokine, other hematopoietic factor, thrombolytic or anti-thrombotic factor, or anti-inflammatory agent.

The pharmaceutical composition of the invention may be in the form of a liposome in which isolated TNF-R1-DD ligand protein or binding inhibitor is combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. No. 4,235,871; U.S. Pat. No. 4,501,728; U.S. Pat. No. 4,837,028; and U.S. Pat. No. 4,737,323, all of which are incorporated herein by reference.

As used herein, the term "therapeutically effective amount" means the total amount of each active component of the pharmaceutical composition or method that is sufficient to show a meaningful patient benefit, i.e., treatment, healing, prevention or amelioration of an inflammatory response or condition, or an increase in rate of treatment, healing, prevention or amelioration of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously.

In practicing the method of treatment or use of the present invention, a therapeutically effective amount of isolated TNF-R1-DD ligand protein or binding inhibitor is administered to a mammal having a condition to be treated. Isolated TNF-R1-DD ligand protein or binding inhibitor may be administered in accordance with the method of the invention either alone or in combination with other therapies such as treatments employing cytokines, lymphokines or other hematopoietic factors. When co-administered with one or more cytokines, lymphokines or other hematopoietic factors, isolated TNF-R1-DD ligand protein or binding inhibitor may be administered either simultaneously with the cytokine(s), lymphokine(s), other hematopoietic factor(s), thrombolytic or anti-thrombotic factors, or sequentially. If administered sequentially, the attending physician will decide on the appropriate sequence of administering isolated TNF-R1-DD ligand protein or binding inhibitor in combination with cytokine(s), lymphokine(s), other hematopoietic factor(s), thrombolytic or anti-thrombotic factors.

Administration of isolated TNF-R1-DD ligand protein or binding inhibitor used in the pharmaceutical composition or to practice the method of the present invention can be carried out in a variety of conventional ways, such as oral ingestion, inhalation, or cutaneous, subcutaneous, or intravenous injection. Intravenous administration to the patient is preferred.

When a therapeutically effective amount of isolated TNF-R1-DD ligand protein or binding inhibitor is administered orally, isolated TNF-R1-DD ligand protein or binding inhibitor will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% isolated TNF-R1-DD ligand protein or binding inhibitor, and preferably from about 25 to 90% isolated TNF-R1-DD ligand protein or binding inhibitor. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of isolated TNF-R1-DD ligand protein or binding inhibitor, and preferably from about 1 to 50% isolated TNF-R1-DD ligand protein or binding inhibitor.

When a therapeutically effective amount of isolated TNF-R1-DD ligand protein or binding inhibitor is administered by intravenous, cutaneous or subcutaneous injection, isolated TNF-R1-DD ligand protein or binding inhibitor will be in the form of a pyrogen-free, parenterally acceptable aqueous solution. The preparation of such parenterally acceptable protein solutions, having due regard to pH, isotonicity, stability, and the like, is within the skill in the art. A preferred pharmaceutical composition for intravenous, cutaneous, or subcutaneous injection should contain, in addition to isolated TNF-R1-DD ligand protein or binding inhibitor, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additives known to those of skill in the art.

The amount of isolated TNF-R1-DD ligand protein or binding inhibitor in the pharmaceutical composition of the present invention will depend upon the nature and severity of the condition being treated, and on the nature of prior treatments which the patient has undergone. Ultimately, the attending physician will decide the amount of isolated TNF-R1-DD ligand protein or binding inhibitor with which to treat each individual patient. Initially, the attending physician will administer low doses of isolated TNF-R1-DD ligand protein or binding inhibitor and observe the patient's response. Larger doses of isolated TNF-R1-DD ligand protein or binding inhibitor may be administered until the optimal therapeutic effect is obtained for the patient, and at that point the dosage is not increased further. It is contemplated that the various pharmaceutical compositions used to practice the method of the present invention should contain about 0.1 $\mu$g to about 100 mg of isolated TNF-R1-DD ligand protein or binding inhibitor per kg body weight.

The duration of intravenous therapy using the pharmaceutical composition of the present invention will vary, depending on the severity of the disease being treated and the condition and potential idiosyncratic response of each individual patient. It is contemplated that the duration of each application of the isolated TNF-R1-DD ligand protein or binding inhibitor will be in the range of 12 to 24 hours of continuous intravenous administration. Ultimately the attending physician will decide on the appropriate duration of intravenous therapy using the pharmaceutical composition of the present invention.

Isolated TNF-R1-DD ligand protein of the invention may also be used to immunize animals to obtain polyclonal and monoclonal antibodies which specifically react with the TNF-R1-DD ligand protein and which may inhibit TNF-R death domain binding. Such antibodies may be obtained using either the entire TNF-R1-DD ligand protein or fragments of TNF-R1-DD ligand protein as an immunogen. The peptide immunogens additionally may contain a cysteine residue at the carboxyl terminus, and are conjugated to a hapten such as keyhole limpet hemocyanin (KLH). Methods for synthesizing such peptides are known in the art, for example, as in R. P. Merrifield, J. Amer.Chem.Soc. 85, 2149–2154 (1963); J. L. Krstenansky, et al., FEBS Lett. 211, 10 (1987).

Monoclonal antibodies binding to TNF-R1-DD ligand protein or to complex carbohydrate moieties characteristic of the TNF-R1-DD ligand glycoprotein may be useful diagnostic agents for the immunodetection of TNF-R ligand protein.

Neutralizing monoclonal antibodies binding to TNF-R1-DD ligand protein or to complex carbohydrates characteristic of TNF-R1-DD ligand glycoprotein may also be useful therapeutics for both inflammatory conditions and also in the treatment of some forms of cancer where abnormal expression of TNF-R1-DD ligand protein is involved. These neutralizing monoclonal antibodies are capable of blocking the signaling function of the TNF-R1-DD ligand protein. By blocking the binding of TNF-R1-DD ligand protein, certain biological responses to TNF are either abolished or markedly reduced. In the case of cancerous cells or leukemic cells, neutralizing monoclonal antibodies against TNF-R1-DD ligand protein may be useful in detecting and preventing the metastatic spread of the cancerous cells, which may be mediated by the TNF-R1-DD ligand protein.

Due to the similarity of their sequences to the insulin growth factor binding protein ("IGFBP-5") and fragments thereof which bind to the TNF-R death domain are proteins having TNF-R1-DD ligand protein activity as defined herein. As a result, they are also useful in pharmaceutical compositions, for treating inflammatory conditions and for inhibiting TNF-R death domain binding as described above for TNF-R1-DD ligand proteins generally.

EXAMPLE 1

Cloning of TNF-R Death Domain Ligand Protein Encoding Polynucleotide

A yeast genetic selection method, the "interaction trap" [Gyuris et al, Cell 75:791–803, 1993, which is incorporated herein by reference], was used to screen W138 cell cDNA libraries (preparation, see below) for proteins that interact with the death domain of the P55 type 1 TNF receptor (TNF-R1-DD). A polynucleotide encoding amino acids 326 to 413 of the P55 type TNF receptor, TNF-R1-DD, was obtained via the polymerase chain reaction (PCR) using a grafting method. This TNF-R1-DD DNA was then cloned into pEG202 by BamHI and SalI sites, generating the bait plasmid, pEG202-TNF-R1-DD. This plasmid contains the HIS3 selectable marker, and expression of the bait, the LexA-TNF-R1-DD fusion protein, is from the strong constitutive ADH1 promoter. To create the reporter strain carrying the bait protein, yeast strain EGY48, containing the reporter sequence LexAop-Leu2 in place of the chromosomal LEU2, was transformed with pEG202-TNF-R1-DD and pSH18–34 (Ura+), which carries another reporter sequence, LexAop-lacZ. For screening cDNAs encoding proteins that interact with TNF-R1-DD, the expression vector pJG4–5 (TRP1), containing the WI38 cell cDNA library (see below for the cDNA library construction), was transformed into the above strain (EGY48/pEG202-TNF-R1-DD/pSH18–34) according to the method described by Gietz et al., Nucleic Acids Res., 20:1425 (1992).

cDNA Library Construction

WI38 cell cDNA library: Double stranded cDNA was prepared from 3 ug of WI38 mRNA using reagents provided by the Superscript Choice System (Gibco/BRL, Gaithersberg, Md.) with the following substitutions: the first strand synthesis was primed using an oligo dT/XhoI primer/linker, and the dNTP mix was substituted with a mix containing methyl dCTP (Stratagene, LaJolla, Calif.). The cDNA was modified at both ends by addition of an EcoRI/NotI/SalI adapter linker and subsequently digested with XhoI. This produced cDNA molecules possessing an EcoRI/NotI/SalI overhang at the 5' end of the gene and an XhoI overhang at the 3' end. These fragments were then ligated into the yeast expression/fusion vector pJG4–5 (Gyuris et al., Cell, 75, 791–803, 1993), which contains at its amino terminus, the influenza virus HA1 epitope tag, the B42 acidic transcription activation domain, and the SV40 nuclear localization signal, all under the control of the galactose-dependent GAL1 promoter. The resulting plasmids were then electroporated into DH10B cells (Gibco/BRL). A total of $7.1 \times 10^6$ colonies were plated on LB plates containing 100 ug/ml of ampicillin. These E.coli were scraped, pooled, and a large scale plasmid prep was performed using the Wizard Maxi Prep kit (Promega, Madison, Wis.), yielding 3.2 mg of supercoiled plasmid DNA.

WI38 Cell cDNA Screening Results $1 \times 10^6$ transformants were obtained on glucose Ura⁻His⁻Trp⁻ plates. These transformants were pooled and resuspended in a solution of 65% glycerol, 10 mM Tris-HCl (pH 7.5), 10 mM $MgCl_2$ and stored at –80° C. in 1 mL aliquots. For screening purposes, aliquots of these were diluted 10-fold into Ura⁻His⁻Trp⁻ CM dropout gal/raff medium (containing 2% galactose, 1% raffinose), which induces the expresssion of the library encoded proteins, and incubated at 30° C. for 4 hours. $12 \times 10^6$ colony forming units (CFUs) were then plated on standard 10 cm galactose X-Gal Ura⁻His⁻Trp⁻Leu⁻ plates at a density of $2 \times 10^5$ CFU/plate. After three days at 30° C., about 1,000 colonies were formed (Leu⁺) and of those, sixty-four colonies were LacZ⁺. In order to test if the Leu⁺/LacZ⁺phenotype was due to the library-encoded protein, the galactose dependency of the phenotype was tested. Expression of the library-encoded proteins was turned off by growth on glucose Ura⁻His⁻Trp⁻ master plates and then retested for galactose-dependency on glucose Ura⁻His⁻Trp⁻Leu⁻, galactose Ura⁻His⁻Trp⁻Leu⁻, glucose X-Gal Ura⁻His⁻Trp⁻, and galactose X-Gal Ura⁻His⁻Trp⁻ plates. Of these, 32 colonies showed galactose-dependent growth on Leu⁻ plates and galactose-dependent blue color on X-Gal-containing medium (LacZ⁺ phenotype). Total yeast DNA was prepared from these colonies according to the method described previously (Hoffman and Winston, 1987). In order to analyze the cDNA sequences, PCR reactions were performed using the above yeast DNA as a template and oligo primers specific for the vector pJG4–5, flanking the cDNA insertion point. PCR products were purified (Qiagen PCR purification kit), subjected to restriction digest with the enzyme HaeIII, run on 1.8% agarose gels, and the restriction patterns compared. Similar and identical restriction patterns were grouped and representatives of each group were sequenced and compared to Genbank and other databases to identify any sequence homologies.

One clone of unique sequence ("2DD") and three clones with identical sequence ("3DD") were isolated and showed no signficant sequence homologies compared to Genbank and other databases. Additionally, four other clones ("20DD") with identical sequence to a portion of human insulin-like growth factor binding protein-5 (Shunichi Shimasaki et al., J. Biol. Chem. 266:10646–10653 (1991)) were isolated. The clones "2DD," "3DD" and "20DD" were chosen for further analysis. Library vector pJG4–5 containing these clones sequences were rescued from yeast by transforming the total yeast DNAs into the E. coli strain KC8 and selecting for growth on Trp-ampicillin plates. These putative TNFR1 interacting proteins were then tested further for specificity of interaction with the TNF-R1-DD by the reintroduction of JG4–5 clone into EGY48 derivatives containing a panel of different baits, including bicoid, the cytoplasmic domain of the IL-1 receptor, and TNF-R1-DD. The above clones were found to interact only with the TNF-R1-DD. The interaction between these clones and TNF-R1-DD was thus judged to be specific.

EXAMPLE 2

Expression of the TNF-R1-DD Ligand Protein cDNAs encoding TNF-R intracellular ligand proteins were released from the pJG4–5 vector with the appropriate restriction enzymes. For example, EcoRI and XhoI or NotI and XhoI were used to release cDNA from clone 2DD and clone 20DD. Where the restriction sites were also present in the internal sequence of the cDNA, PCR was performed to obtain the cDNA. For example, the cDNA fragment encoding "clone 3DD" was obtained through PCR due to the presence of an internal XhoI site. These cDNAs were then cloned into various expression vectors. These included pGEX (Pharmacia) or pMAL (New England Biolabs) for expression as a GST (Glutathione-S-transferase) or MBP (maltose binding protein) fusion protein in E. coli, a pED-based vector for mammalian expression, and pVL or pBlueBacHis (Invitrogen) for baculovirus/insect expression. For the immunodetection of TNF-R intracellular ligand expression in mammalian cells, an epitope sequence, "Flag," (SEQ ID NO: 9) was inserted into the translational start site of the pED vector, generating the pED-Flag vector. cDNAs were then inserted into the pED-Flag vector. Thus, the expression of cDNA from pED-Flag yields a protein with an amino terminal Met, followed by the "Flag" sequence, Asp-Tyr-Lys-Asp-Asp-Asp-Asp-Lys (SEQ ID NO: 9). Standard DEAE-Dextran or lipofectamine methods were used to transfect COS or CHO dukx cells. Immunodetection of Flag-tagged proteins was achieved using the M2 antibody (Kodak). Moreover, an immunoaffinity column using the M2 antibody, followed by elution with the "Flag" (SEQ ID NO: 9) peptide, can be used for the rapid purification of the flag-tagged protein. Similarly, affinity purification of GST-, MBP- or His-tagged fusion proteins can be performed using glutathione, amylose, or nickel columns. Detailed purification protocols are provided by the manufacturers. For many fusion proteins, the TNF-R intracellular ligand can be released by the action of thrombin, factor Xa, or enterokinase cleavage. In the case where highly purified material is required, standard purification procedures, such as ion-exchange, hydrophobic, and gel filtration chromatography will be applied in addition to the affinity purification step.

Figure 1:
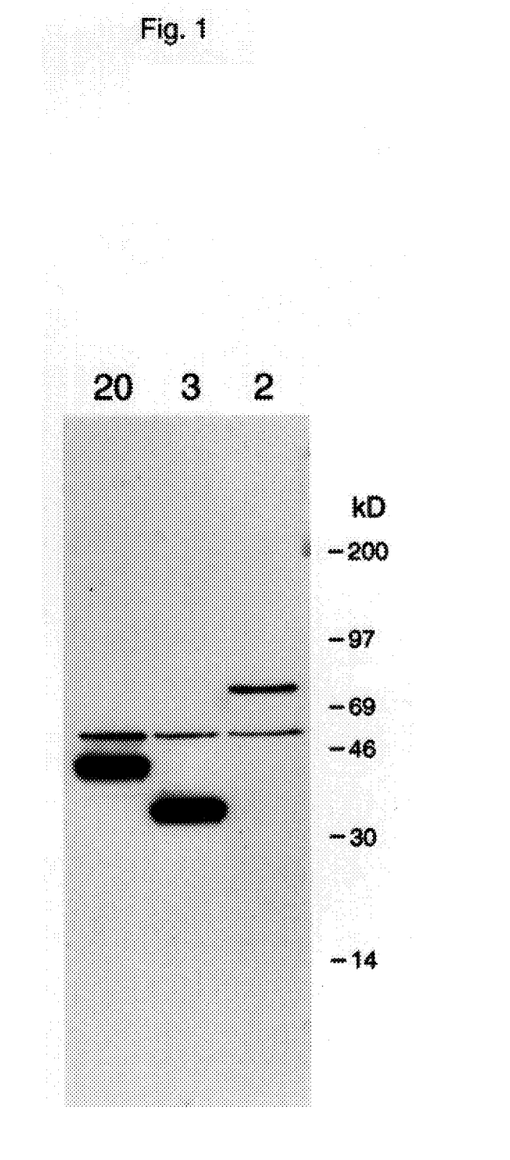
FIGS. 1 and 2 depict autoradiographs demonstrating the expression of TNF-R1-DD ligand proteins of the present invention.
Figure 2:
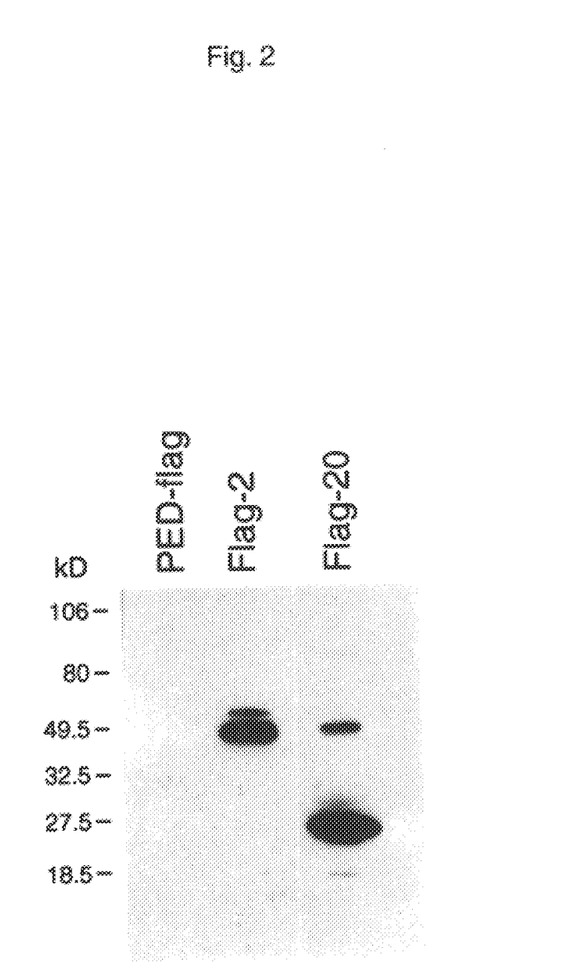

FIGS. 1 and 2 depict autoradiographs demonstrating the expression of TNF-R1-DD ligand proteins in yeast and mammalian cells. FIG. 1 shows the results of expression of isloated clones of the present invention in yeast. EGY48 was transformed with pJG4–5 containing clone 2DD, 3DD or 20DD. Cells were then grown overnight in the galactose/ raffinose medium. Cell lysates were prepared and subject to 4–20% SDS gel electrophoresis, followed by Western blot analysis using anti-HA antibody (12CA5, Boehringer Mannheim, Indianapolis, Ind.). FIG. 2 shows the results of expression of Flag-2DD and Flag-20DD in COS cells. COS cells were transfected with either pED-Flag (Vector control), Flag-2DD or Flag-20DD plasmid by the lipofectamine method. Thirty µg of each cell lysate were prepared and subjected to 4–20% SDS gel electrophoresis, followed by Western blot analysis using M2 antibody (Kodak). The bands in the Flag-2DD and Flag-20DD lanes indicate significant expression of the respective TNF-R1-DD ligand proteins.

EXAMPLE 3

Assays of TNF-R Death Domain Binding

Two different methods were used to assay for TNF-R1-DD ligand protein activity. The first assay measures binding in the yeast strain in "interaction trap," the system used here to screen for TNF-R1-DD interacting proteins. In this system, the expression of reporter genes from both LexAop-Leu2 and LexAop-LacZ relies on the interaction between the bait protein, in this case TNF-R1DD, and the prey, the TNF-R intracellular ligand. Thus, one can measure the strength of the interaction by the level of Leu2 or LacZ expression. The most simple method is to measure the activity of the LacZ encoded protein, β-galactosidase. This activity can be judged by the degree of blueness on the X-Gal containing medium or filter. For the quantitative measurement of β-galactosidase activity, standard assays can be found in "Methods in Yeast Genetics" Cold Spring Harbor, N.Y., 1990 (by Rose, M. D., Winston, F., and Hieter, P.).

The second assay for measuring binding is a cell-free system. An example of a typical assay is described below. Purified GST-TNF-R1-DD fusion protein (2 ug) was mixed with amylose resins bound with a GST-TNF-R1-DD intracellular ligand for 2 hour at 4° C. The mixture was then centrifuged to separate bound (remained with the beads) and unbound (remained in the supernatant) GST-TNF-R1-DD. After extensive washing, the bound GST-TNF-R1-DD was eluted with maltose and detected by Western blot analysis using a GST antibody. The TNF-R1-DD or the intracellular ligand can also be immobilized on other solid supports, such as on plates or fluorobeads. The binding can then be measured using ELISA or SPA (scintillation proximity assay).

EXAMPLE 4

Characterization of TNF-R Death Domain Ligand Protein

Mapping the Interaction Site in TNF-R1

Many of the key amino acids for TNF-R signaling have been determined by site-directed mutagenesis (Tataglia et al., Cell 74:845–853 (1993). These amino acids are conserved between TNF-R and the Fas antigen, which is required for mediating cytotoxicity and other cellular responses. In order to test if the TNF-R intracellular proteins interact with these residues, the following mutations were constructed: F345A (substitution of phe at amino acid 345 to Ala), R347A, L351A, F345A/R347A/L351A, E369A, W378A and I408A. The ability of the mutant protein to interact with the intracellular ligand in the "interaction trap" system was tested.

Effect on the TNF-mediated Response

The effect of the TNF-R intracellular ligands on the TNF-mediated response can be evaluated in cells overexpressing the ligands. A number of TNF-mediated responses, including transient or prolonged responses, can be measured. For example, TNF-induced kinase activity toward either MBP (myelin basic protein) or the N-terminus (amino acids 1–79) of c-jun can be measured in COS cells or CHO cells either transiently or stably overexpressing clone 2DD, 3DD or clone 20DD. The significance of these ligand proteins in TNF-mediated cytotoxicity and other cellular responses can be measured in L929 or U937 overexpressing cells. Alternatively, other functional assays, such as the induction of gene expression or $PGE_2$ production after prolonged incubation with TNF, can also be used to measure the TNF mediated response. Conversely, the significance of the TNF-R1-DD ligand proteins in TNF signaling can be established by lowering or eliminating the expression of the ligands. These experiments can be performed using antisense expression or transgenic mice.

Enzymatic or Functional Assays

The signal transduction events initiated by TNF binding to its receptor are still largely unknown. However, one major result of TNF binding is the stimulation of cellular serine/ threonine kinase activity. In addition, TNF has been shown to stimulate the activity of PC-PLC, $PLA_2$, and sphingomyelinase. Therefore, some of the TNF-R1-DD ligand proteins may possess intrinsic enzymatic activity that is responsible for these activities. Therefore, enzymatic assays can be performed to test this possibility, particularly with those clones that encode proteins with sequence homology to known enzymes. In addition to enzymatic activity, based on the sequence homology to proteins with known function, other functional assays can also be measured.

EXAMPLE 5

Isolation of Full Length Clones

In many cases, cDNAs obtained from the interaction trap method each encode only a portion of the full length protein. For example, based on identity and sequence and the lack of the initiating methionine codon, clones 2DD, 3DD and 20DD apparently do not encode full length proteins. Therefore, it is desirable to isolate full length clones. The cDNAs obtained from the screening, such as clone 2DD, are used as probes, and the cDNA libraries described herein, or alternatively phage cDNA libraries, are screened to obtain full length clones in accordance with known methods (see for example, "Molecular Cloning, A Laboratory Manual", by Sambrook et al., 1989 Cold Spring Harbor).

EXAMPLE 6

Antibodies Specific for TNF-R Intracellular Ligand Protein

Antibodies specific for TNF-R intracellular ligand proteins can be produced using purified recombinant protein, as described in Example 2, as antigen. Both polyclonal and monoclonal antibodies will be produced using standard techniques, such as those described in "Antibodies, a Laboratory Manual" by Ed Harlow and David Lane (1988), Cold Spring Harbor Laboratory.

---

What is claimed is:

1. An isolated polynucleotide selected from the group consisting of:
   (a) a polynucleotide comprising a fragment of the nucleotide sequence of SEQ ID NO:3, wherein said fragment encodes a protein having TNF-R1-DD ligand protein activity; and
   (b) a polynucleotide encoding a TNF-R1-DD ligand protein comprising a fragment of the amino acid sequence of SEQ ID NO:4, wherein said fragment has TNF-R1-DD ligand protein activity.

2. A polynucleotide of claim 1 wherein said polynucleotide is operably linked to an expression control sequence.

3. A host cell transformed with a polynucleotide of claim 2.

4. The host cell of claim 3 wherein said cell is a mammalian cell.

5. A process for producing a TNF-R1-DD ligand protein, which comprises:
   (a) growing a culture of the host cell of claim 3 in a suitable culture medium; and
   (b) purifying the TNF-R1-DD ligand protein from the culture.

6. An isolated polynucleotide encoding a protein having TNF-R1-DD ligand protein activity, said polynucleotide comprising the nucleotide sequence of SEQ ID NO:3 from nucleotide 2 to nucleotide 415.

7. A polynucleotide of claim 6 wherein said polynucleotide is operably linked to an expression control sequence.

8. A host cell transformed with a polynucleotide of claim 7.

9. The host cell of claim 8, wherein said cell is a mammalian cell.

10. A process for producing a TNF-R1-DD ligand protein, which comprises:
   (a) growing a culture of the host cell of claim 8 in a suitable culture medium; and
   (b) purifying the TNF-R1-DD ligand protein from the culture.

11. An isolated polynucleotide encoding a protein having TNF-R1-DD ligand protein activity, said protein comprising the amino acid sequence of SEQ ID NO:4.

12. A polynucleotide of claim 11 wherein said polynucleotide is operably linked to an expression control sequence.

13. A host cell transformed with a polynucleotide of claim 12.

14. The host cell of claim 13, wherein said cell is a mammalian cell.

15. A process for producing a TNF-R1-DD ligand protein, which comprises:
   (a) growing a culture of the host cell of claim 13 in a suitable culture medium; and
   (b) purifying the TNF-R1-DD ligand protein from the culture.

* * * * *

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 2158 base pairs
        ( B ) TYPE: nucleic acid
        ( C ) STRANDEDNESS: double
        ( D ) TOPOLOGY: linear     ( i i ) MOLECULE TYPE: cDNA     ( i i i ) HYPOTHETICAL: NO     ( i x ) FEATURE:
        ( A ) NAME/KEY: CDS
        ( B ) LOCATION: 2..1231

( x i ) SEQUENCE DESCRIPTION: SEQ ID NO:1:

```
C  AGC  AAT  GCA  GGT  GAT  GGA  CCA  GGT  GGC  GAG  GGC  AGT  GTT  CAC  CTG           46
   Ser  Asn  Ala  Gly  Asp  Gly  Pro  Gly  Gly  Glu  Gly  Ser  Val  His  Leu
   1                 5                        10                        15

GCA  AGC  TCT  CGG  GGC  ACT  TTG  TCT  GAT  AGT  GAA  ATT  GAG  ACC  AAC  TCT           94
Ala  Ser  Ser  Arg  Gly  Thr  Leu  Ser  Asp  Ser  Glu  Ile  Glu  Thr  Asn  Ser
                    20                       25                       30

GCC  ACA  AGC  ACC  ATC  TTT  GGT  AAA  GCC  CAC  AGC  TTG  AAG  CCA  AGC  ATA          142
Ala  Thr  Ser  Thr  Ile  Phe  Gly  Lys  Ala  His  Ser  Leu  Lys  Pro  Ser  Ile
               35                       40                       45

AAG  GAG  AAG  CTG  GCA  GGC  AGC  CCC  ATT  CGT  ACT  TCT  GAA  GAT  GTG  AGC          190
Lys  Glu  Lys  Leu  Ala  Gly  Ser  Pro  Ile  Arg  Thr  Ser  Glu  Asp  Val  Ser
          50                       55                       60

CAG  CGA  GTC  TAT  CTC  TAT  GAG  GGA  CTC  CTA  GGC  AAA  GAG  CGT  TCT  ACT          238
Gln  Arg  Val  Tyr  Leu  Tyr  Glu  Gly  Leu  Leu  Gly  Lys  Glu  Arg  Ser  Thr
     65                       70                       75

TTA  TGG  GAC  CAA  ATG  CAA  TTC  TGG  GAA  GAT  GCC  TTC  TTA  GAT  GCT  GTG          286
Leu  Trp  Asp  Gln  Met  Gln  Phe  Trp  Glu  Asp  Ala  Phe  Leu  Asp  Ala  Val
80                       85                       90                       95

ATG  TTG  GAG  AGA  GAA  GGG  ATG  GGT  ATG  GAC  CAG  GGT  CCC  CAG  GAA  ATG          334
Met  Leu  Glu  Arg  Glu  Gly  Met  Gly  Met  Asp  Gln  Gly  Pro  Gln  Glu  Met
                    100                      105                      110

ATC  GAC  AGG  TAC  CTG  TCC  CTT  GGA  GAA  CAT  GAC  CGG  AAG  CGC  CTG  GAA          382
Ile  Asp  Arg  Tyr  Leu  Ser  Leu  Gly  Glu  His  Asp  Arg  Lys  Arg  Leu  Glu
               115                      120                      125

GAT  GAT  GAA  GAT  CGC  TTG  CTG  GCC  ACA  CTT  CTG  CAC  AAC  CTC  ATC  TCC          430
Asp  Asp  Glu  Asp  Arg  Leu  Leu  Ala  Thr  Leu  Leu  His  Asn  Leu  Ile  Ser
          130                      135                      140

TAC  ATG  CTG  CTG  ATG  AAG  GTA  AAT  AAG  AAT  GAC  ATC  CGC  AAG  AAG  GTG          478
Tyr  Met  Leu  Leu  Met  Lys  Val  Asn  Lys  Asn  Asp  Ile  Arg  Lys  Lys  Val
     145                      150                      155

AGG  CGC  CTA  ATG  GGA  AAG  TCG  CAC  ATT  GGG  CTT  GTG  TAC  AGC  CAG  CAA          526
Arg  Arg  Leu  Met  Gly  Lys  Ser  His  Ile  Gly  Leu  Val  Tyr  Ser  Gln  Gln
160                      165                      170                      175

ATC  AAT  GAG  GTG  CTT  GAT  CAG  CTG  GCG  AAC  CTG  AAT  GGA  CGC  GAT  CTC          574
Ile  Asn  Glu  Val  Leu  Asp  Gln  Leu  Ala  Asn  Leu  Asn  Gly  Arg  Asp  Leu
                    180                      185                      190

TCT  ATC  TGG  TCC  AGT  GGC  AGC  CGG  CAC  ATG  AAG  AAG  CAG  ACA  TTT  GTG          622
Ser  Ile  Trp  Ser  Ser  Gly  Ser  Arg  His  Met  Lys  Lys  Gln  Thr  Phe  Val
               195                      200                      205

GTA  CAT  GCA  GGG  ACA  GAT  ACA  AAC  GGA  GAT  ATC  TTT  TTC  ATG  GAG  GTG          670
Val  His  Ala  Gly  Thr  Asp  Thr  Asn  Gly  Asp  Ile  Phe  Phe  Met  Glu  Val
```

```
                       210                          215                          220
TGC  GAT  GAC  TGT  GTG  GTG  TTG  CGT  AGT  AAC  ATC  GGA  ACA  GTG  TAT  GAG                  718
Cys  Asp  Asp  Cys  Val  Val  Leu  Arg  Ser  Asn  Ile  Gly  Thr  Val  Tyr  Glu
     225                      230                     235

CGC  TGG  TGG  TAC  GAG  AAG  CTC  ATC  AAC  ATG  ACC  TAC  TGT  CCC  AAG  ACG                  766
Arg  Trp  Trp  Tyr  Glu  Lys  Leu  Ile  Asn  Met  Thr  Tyr  Cys  Pro  Lys  Thr
240                      245                     250                           255

AAG  GTG  TTG  TGC  TTG  TGG  CGT  AGA  AAT  GGC  TCT  GAG  ACC  CAG  CTC  AAC                  814
Lys  Val  Leu  Cys  Leu  Trp  Arg  Arg  Asn  Gly  Ser  Glu  Thr  Gln  Leu  Asn
                    260                      265                          270

AAG  TTC  TAT  ACT  AAA  AAG  TGT  CGG  GAG  CTG  TAC  TAC  TGT  GTG  AAG  GAC                  862
Lys  Phe  Tyr  Thr  Lys  Lys  Cys  Arg  Glu  Leu  Tyr  Tyr  Cys  Val  Lys  Asp
               275                      280                     285

AGC  ATG  GAG  CGC  GCT  GCC  GCC  CGA  CAG  CAA  AGC  ATC  AAA  CCC  GGA  CCT                  910
Ser  Met  Glu  Arg  Ala  Ala  Ala  Arg  Gln  Gln  Ser  Ile  Lys  Pro  Gly  Pro
          290                      295                          300

GAA  TTG  GGT  GGC  GAG  TTC  CCT  GTG  CAG  GAC  CTG  AAG  ACT  GGT  GAG  GGT                  958
Glu  Leu  Gly  Gly  Glu  Phe  Pro  Val  Gln  Asp  Leu  Lys  Thr  Gly  Glu  Gly
     305                      310                     315

GGC  CTG  CTG  CAG  GTG  ACC  CTG  GAA  GGG  ATC  AAC  CTC  AAA  TTC  ATG  CAC                 1006
Gly  Leu  Leu  Gln  Val  Thr  Leu  Glu  Gly  Ile  Asn  Leu  Lys  Phe  Met  His
320                      325                     330                           335

AAT  CAG  GTT  TTC  ATA  GAG  CTG  AAT  CAC  ATT  AAA  AAG  TGC  AAT  ACA  GTT                 1054
Asn  Gln  Val  Phe  Ile  Glu  Leu  Asn  His  Ile  Lys  Lys  Cys  Asn  Thr  Val
                    340                      345                         350

CGA  GGC  GTC  TTT  GTC  CTG  GAG  GAA  TTT  GTT  CCT  GAA  ATT  AAA  GAA  GTG                 1102
Arg  Gly  Val  Phe  Val  Leu  Glu  Glu  Phe  Val  Pro  Glu  Ile  Lys  Glu  Val
               355                      360                     365

GTG  AGC  CAC  AAG  TAC  AAG  ACA  CCA  ATG  GCC  CAC  GAA  ATC  TGC  TAC  TCC                 1150
Val  Ser  His  Lys  Tyr  Lys  Thr  Pro  Met  Ala  His  Glu  Ile  Cys  Tyr  Ser
          370                      375                          380

GTA  TTA  TGT  CTC  TTC  TCG  TAC  GTG  GCT  GCA  GTT  CAT  AGC  AGT  GAG  GAA                 1198
Val  Leu  Cys  Leu  Phe  Ser  Tyr  Val  Ala  Ala  Val  His  Ser  Ser  Glu  Glu
     385                      390                     395

GAT  CTC  AGA  ACC  CCG  CCC  CGG  CCT  GTC  TCT  AGC  TGATGGAGAG  GGGCTACGCA                  1251
Asp  Leu  Arg  Thr  Pro  Pro  Arg  Pro  Val  Ser  Ser
400                      405                     410

GCTGCCCCAG  CCCAGGGCAC  GCCCCTGGCC  CCTTGCTGTT  CCCAAGTGCA  CGATGCTGCT                          1311

GTGACTGAGG  AGTGGATGAT  GCTCGTGTGT  CCTCTGCAAG  CCCCCTGCTG  TGGCTTGGGT                          1371

GGGTACCGGT  TATGTGTCCC  TCTGAGTGTG  TCTTGAGCGT  GTCCACCTTC  TCCCTCTCCA                          1431

CTCCCAGAAG  ACCAAACTGC  CTTCCCCTCA  GGGCTCAAGA  ATGTGTACAG  TCTGTGGGGC                          1491

CGGTGTGAAC  CCACTATTTT  GTGTCCTTGA  CACATTTGTG  TTGTGGTTCC  TTGTCCTTGT                          1551

CCCTGGCGTT  AACTGTCCAC  TGCAAGAGTC  TGGCTCTCCC  TTCTCTGTGA  CCCGGCATGA                          1611

CTGGGCGCCT  GGAGCAGTTT  CACTCTGTGA  GGAGTGAGGG  AACCCTGGGG  CTCACCCTCT                          1671

CAGAGGAAGG  GCACAGAGAG  GAAGGGAAGA  ATTGGGGGGC  AGCCGGAGTG  AGTGGCAGCC                          1731

TCCCTGCTTC  CTTCTGCATT  CCCAAGCCGG  CAGCTACTGC  CCAGGGCCCG  CAGTGTTGGC                          1791

TGCTGCCTGC  CACAGCCTCT  GTGACTGCAG  TGGAGCGGCG  AATTCCCTGT  GGCCTGCCAC                          1851

GCCTTCGGCA  TCAGAGGATG  GAGTGGTCGA  GGCTAGTGGA  GTCCCAGGGA  CCGCTGGCTG                          1911

CTCTGCCTGA  GCATCAGGGA  GGGGCAGGA   AAGACCAAGC  TGGGTTTGCA  CATCTGTCTG                          1971

CAGGCTGTCT  CTCCAGGCAC  GGGGTGTCAG  GAGGGAGAGA  CAGCCTGGGT  ATGGGCAAGA                          2031

AATGACTGTA  AATATTTCAG  CCCCACATTA  TTTATAGAAA  ATGTACAGTT  GTGTGAATGT                          2091

GAAATAAATG  TCCTCACCTC  CCAAAAAAAA  AAAAAAAAAA  AAAAAAAAAA  AAAAAAAAA                           2151
```

AAAAAA 2158

(2) INFORMATION FOR SEQ ID NO:2:

(i) SEQUENCE CHARACTERISTICS:
        (A) LENGTH: 410 amino acids
        (B) TYPE: amino acid
        (D) TOPOLOGY: linear     (ii) MOLECULE TYPE: protein     (xi) SEQUENCE DESCRIPTION: SEQ ID NO:2:

```
Ser Asn Ala Gly Asp Gly Pro Gly Gly Glu Gly Ser Val His Leu Ala
 1               5                  10                  15
Ser Ser Arg Gly Thr Leu Ser Asp Ser Glu Ile Glu Thr Asn Ser Ala
             20                  25                  30
Thr Ser Thr Ile Phe Gly Lys Ala His Ser Leu Lys Pro Ser Ile Lys
         35                  40                  45
Glu Lys Leu Ala Gly Ser Pro Ile Arg Thr Ser Glu Asp Val Ser Gln
     50                  55                  60
Arg Val Tyr Leu Tyr Glu Gly Leu Leu Gly Lys Glu Arg Ser Thr Leu
65                  70                  75                  80
Trp Asp Gln Met Gln Phe Trp Glu Asp Ala Phe Leu Asp Ala Val Met
                 85                  90                  95
Leu Glu Arg Glu Gly Met Gly Met Asp Gln Gly Pro Gln Glu Met Ile
                100                 105                 110
Asp Arg Tyr Leu Ser Leu Gly Glu His Asp Arg Lys Arg Leu Glu Asp
            115                 120                 125
Asp Glu Asp Arg Leu Leu Ala Thr Leu Leu His Asn Leu Ile Ser Tyr
        130                 135                 140
Met Leu Leu Met Lys Val Asn Lys Asn Asp Ile Arg Lys Lys Val Arg
145                 150                 155                 160
Arg Leu Met Gly Lys Ser His Ile Gly Leu Val Tyr Ser Gln Gln Ile
                165                 170                 175
Asn Glu Val Leu Asp Gln Leu Ala Asn Leu Asn Gly Arg Asp Leu Ser
                180                 185                 190
Ile Trp Ser Ser Gly Ser Arg His Met Lys Lys Gln Thr Phe Val Val
            195                 200                 205
His Ala Gly Thr Asp Thr Asn Gly Asp Ile Phe Phe Met Glu Val Cys
        210                 215                 220
Asp Asp Cys Val Val Leu Arg Ser Asn Ile Gly Thr Val Tyr Glu Arg
225                 230                 235                 240
Trp Trp Tyr Glu Lys Leu Ile Asn Met Thr Tyr Cys Pro Lys Thr Lys
                245                 250                 255
Val Leu Cys Leu Trp Arg Arg Asn Gly Ser Glu Thr Gln Leu Asn Lys
                260                 265                 270
Phe Tyr Thr Lys Lys Cys Arg Glu Leu Tyr Tyr Cys Val Lys Asp Ser
            275                 280                 285
Met Glu Arg Ala Ala Ala Arg Gln Gln Ser Ile Lys Pro Gly Pro Glu
        290                 295                 300
Leu Gly Gly Glu Phe Pro Val Gln Asp Leu Lys Thr Gly Glu Gly Gly
305                 310                 315                 320
Leu Leu Gln Val Thr Leu Glu Gly Ile Asn Leu Lys Phe Met His Asn
                325                 330                 335
Gln Val Phe Ile Glu Leu Asn His Ile Lys Lys Cys Asn Thr Val Arg
            340                 345                 350
```

```
Gly  Val  Phe  Val  Leu  Glu  Glu  Phe  Val  Pro  Glu  Ile  Lys  Glu  Val  Val
          355                      360                     365

Ser  His  Lys  Tyr  Lys  Thr  Pro  Met  Ala  His  Glu  Ile  Cys  Tyr  Ser  Val
          370                      375                     380

Leu  Cys  Leu  Phe  Ser  Tyr  Val  Ala  Ala  Val  His  Ser  Ser  Glu  Glu  Asp
385                      390                     395                          400

Leu  Arg  Thr  Pro  Pro  Arg  Pro  Val  Ser  Ser
                    405                      410
```

( 2 ) INFORMATION FOR SEQ ID NO:3:

( i ) SEQUENCE CHARACTERISTICS:
        ( A ) LENGTH: 826 base pairs
        ( B ) TYPE: nucleic acid
        ( C ) STRANDEDNESS: double
        ( D ) TOPOLOGY: linear     ( i i ) MOLECULE TYPE: cDNA     ( i i i ) HYPOTHETICAL: NO     ( i x ) FEATURE:
        ( A ) NAME/KEY: CDS
        ( B ) LOCATION: 2..415

( x i ) SEQUENCE DESCRIPTION: SEQ ID NO:3:

```
G  GAG  GTG  CAG  GAC  CTC  TTC  GAA  GCC  CAG  GGC  AAT  GAC  CGA  CTG  AAG       46
   Glu  Val  Gln  Asp  Leu  Phe  Glu  Ala  Gln  Gly  Asn  Asp  Arg  Leu  Lys
   1                   5                        10                      15

CTG  CTG  GTG  CTG  TAC  AGT  GGA  GAG  GAT  GAT  GAG  CTG  CTA  CAG  CGG  GCA     94
Leu  Leu  Val  Leu  Tyr  Ser  Gly  Glu  Asp  Asp  Glu  Leu  Leu  Gln  Arg  Ala
                    20                       25                      30

GCT  GCC  GGG  GGC  TTG  GCC  ATG  CTT  ACC  TCC  ATG  CGG  CCC  ACG  CTC  TGC    142
Ala  Ala  Gly  Gly  Leu  Ala  Met  Leu  Thr  Ser  Met  Arg  Pro  Thr  Leu  Cys
               35                       40                       45

AGC  CGC  ATT  CCC  CAA  GTG  ACC  ACA  CAC  TGG  CTG  GAG  ATC  CTG  CAG  GCC    190
Ser  Arg  Ile  Pro  Gln  Val  Thr  Thr  His  Trp  Leu  Glu  Ile  Leu  Gln  Ala
          50                       55                       60

CTG  CTT  CTG  AGC  TCC  AAC  CAG  GAG  CTG  CAG  CAC  CGG  GGT  GCT  GTG  GTG    238
Leu  Leu  Leu  Ser  Ser  Asn  Gln  Glu  Leu  Gln  His  Arg  Gly  Ala  Val  Val
     65                       70                       75

GTG  CTG  AAC  ATG  GTG  GAG  GCC  TCG  AGG  GAG  ATT  GCC  AGC  ACC  CTG  ATG    286
Val  Leu  Asn  Met  Val  Glu  Ala  Ser  Arg  Glu  Ile  Ala  Ser  Thr  Leu  Met
80                       85                       90                      95

GAG  AGT  GAG  ATG  ATG  GAG  ATC  TTG  TCA  GTG  CTA  GCT  AAG  GGT  GAC  CAC    334
Glu  Ser  Glu  Met  Met  Glu  Ile  Leu  Ser  Val  Leu  Ala  Lys  Gly  Asp  His
                    100                      105                     110

AGC  CCT  GTC  ACA  AGG  GCT  GCT  GCA  GCC  TGC  CTG  GAC  AAA  GCA  GTG  GAA    382
Ser  Pro  Val  Thr  Arg  Ala  Ala  Ala  Ala  Cys  Leu  Asp  Lys  Ala  Val  Glu
               115                      120                     125

TAT  GGG  CTT  ATC  CAA  CCC  AAC  CAA  GAT  GGA  GAG  TGAGGGGTT   GTCCCTGGGC      435
Tyr  Gly  Leu  Ile  Gln  Pro  Asn  Gln  Asp  Gly  Glu
          130                      135

CCAAGGCTCA  TGCACACGCT  ACCTATTGTG  GCACGGAGAG  TAAGGACGGA  AGCAGCTTTG             495

GCTGGTGGTG  GCTGGCATGC  CCAATACTCT  TGCCCATCCT  CGCTTGCTGC  CCTAGGATGT             555

CCTCTGTTCT  GAGTCAGCGG  CCACGTTCAG  TCACACAGCC  CTGCTTGGCC  AGCACTGCCT             615

GCAGCCTCAC  TCAGAGGGGC  CCTTTTTCTG  TACTACTGTA  GTCAGCTGGG  AATGGGGAAG             675

GTGCATCCCA  ACACAGCCTG  TGGATCCTGG  GGCATTTGGA  AGGGCGCACA  CATCAGCAGC             735

CTCACCAGCT  GTGAGCCTGC  TATCAGGCCT  GCCCCTCCAA  TAAAAGTGTG  TAGAACTCCA             795

AAAAAAAAAA  AAAAAAAAAA  AAAAAAAAA   A                                              826
```

(2) INFORMATION FOR SEQ ID NO:4:

(i) SEQUENCE CHARACTERISTICS:
        (A) LENGTH: 138 amino acids
        (B) TYPE: amino acid
        (D) TOPOLOGY: linear     (ii) MOLECULE TYPE: protein     (xi) SEQUENCE DESCRIPTION: SEQ ID NO:4:

```
Glu Val Gln Asp Leu Phe Glu Ala Gln Gly Asn Asp Arg Leu Lys Leu
  1               5                  10                  15

Leu Val Leu Tyr Ser Gly Glu Asp Glu Leu Leu Gln Arg Ala Ala
             20                  25                  30

Ala Gly Gly Leu Ala Met Leu Thr Ser Met Arg Pro Thr Leu Cys Ser
             35                  40                  45

Arg Ile Pro Gln Val Thr Thr His Trp Leu Glu Ile Leu Gln Ala Leu
         50                  55                  60

Leu Leu Ser Ser Asn Gln Glu Leu Gln His Arg Gly Ala Val Val Val
 65                  70                  75                  80

Leu Asn Met Val Glu Ala Ser Arg Glu Ile Ala Ser Thr Leu Met Glu
                 85                  90                  95

Ser Glu Met Met Glu Ile Leu Ser Val Leu Ala Lys Gly Asp His Ser
                100                 105                 110

Pro Val Thr Arg Ala Ala Ala Ala Cys Leu Asp Lys Ala Val Glu Tyr
            115                 120                 125

Gly Leu Ile Gln Pro Asn Gln Asp Gly Glu
            130                 135
```

(2) INFORMATION FOR SEQ ID NO:5:

(i) SEQUENCE CHARACTERISTICS:
        (A) LENGTH: 722 base pairs
        (B) TYPE: nucleic acid
        (C) STRANDEDNESS: double
        (D) TOPOLOGY: linear     (ii) MOLECULE TYPE: cDNA     (iii) HYPOTHETICAL: NO     (ix) FEATURE:
        (A) NAME/KEY: CDS
        (B) LOCATION: 2..559

(xi) SEQUENCE DESCRIPTION: SEQ ID NO:5:

```
G GAG AAG CCG CTG CAC GCC CTG CTG CAC GGC CGC GGG GTT TGC CTC        46
  Glu Lys Pro Leu His Ala Leu Leu His Gly Arg Gly Val Cys Leu
   1               5                  10                  15

AAC GAA AAG AGC TAC CGC GAG CAA GTC AAG ATC GAG AGA GAC TCC CGT      94
Asn Glu Lys Ser Tyr Arg Glu Gln Val Lys Ile Glu Arg Asp Ser Arg
                 20                  25                  30

GAG CAC GAG GAG CCC ACC ACC TCT GAG ATG GCC GAG GAG ACC TAC TCC     142
Glu His Glu Glu Pro Thr Thr Ser Glu Met Ala Glu Glu Thr Tyr Ser
             35                  40                  45

CCC AAG ATC TTC CGG CCC AAA CAC ACC CGC ATC TCC GAG CTG AAG GCT     190
Pro Lys Ile Phe Arg Pro Lys His Thr Arg Ile Ser Glu Leu Lys Ala
         50                  55                  60

GAA GCA GTG AAG AAG GAC CGC AGA AAG AAG CTG ACC CAG TCC AAG TTT     238
Glu Ala Val Lys Lys Asp Arg Arg Lys Lys Leu Thr Gln Ser Lys Phe
 65                  70                  75

GTC GGG GGA GCC GAG AAC ACT GCC CAC CCC GGA TCA TCT CT GAA CCT      286
```

```
Val  Gly  Gly  Ala  Glu  Asn  Thr  Ala  His  Pro  Arg  Ile  Ile  Ser  Glu  Pro
 80                       85                       90                       95

GAG  ATG  AGA  CAG  GAG  TCT  GAG  CAG  GGC  CCC  TGC  CGC  AGA  CAC  ATG  GAG    334
Glu  Met  Arg  Gln  Glu  Ser  Glu  Gln  Gly  Pro  Cys  Arg  Arg  His  Met  Glu
                         100                      105                      110

GCT  TCC  CTG  CAG  GAG  CTC  AAA  GCC  AGC  CCA  CGC  ATG  GTG  CCC  CGT  GCT    382
Ala  Ser  Leu  Gln  Glu  Leu  Lys  Ala  Ser  Pro  Arg  Met  Val  Pro  Arg  Ala
                    115                      120                      125

GTG  TAC  CTG  CCC  AAT  TGT  GAC  CGC  AAA  GGA  TTC  TAC  AAG  AGA  AAG  CAG    430
Val  Tyr  Leu  Pro  Asn  Cys  Asp  Arg  Lys  Gly  Phe  Tyr  Lys  Arg  Lys  Gln
               130                      135                      140

TGC  AAA  CCT  TCC  CGT  GGC  CGC  AAG  CGT  GGC  ATC  TGC  TGG  TGC  GTG  GAC    478
Cys  Lys  Pro  Ser  Arg  Gly  Arg  Lys  Arg  Gly  Ile  Cys  Trp  Cys  Val  Asp
     145                      150                      155

AAG  TAC  GGG  ATG  AAG  CTG  CCA  GGC  ATG  GAG  TAC  GTT  GAC  GGG  GAC  TTT    526
Lys  Tyr  Gly  Met  Lys  Leu  Pro  Gly  Met  Glu  Tyr  Val  Asp  Gly  Asp  Phe
160                      165                      170                      175

CAG  TGC  CAC  ACC  TTC  GAC  AGC  AGC  AAC  GTT  GAG  TGATGCGTCC CCCCCCAACC       579
Gln  Cys  His  Thr  Phe  Asp  Ser  Ser  Asn  Val  Glu
                    180                      185

TTTCCCTCAC CCCCTTCCAC CCCCAGCCCC GACTCCAGCC AGCGCCTCCC TCCACCCCAG                  639

GACGCCACTC ATTTCATCTC ATTTAAGGGA AAAATATATA TCTATCTATT TGAGGAAAAA                  699

AAAAAAAAAA AAAAAAAAAA AAA                                                          722
```

( 2 ) INFORMATION FOR SEQ ID NO:6:

( i ) SEQUENCE CHARACTERISTICS:
        ( A ) LENGTH: 186 amino acids
        ( B ) TYPE: amino acid
        ( D ) TOPOLOGY: linear     ( i i ) MOLECULE TYPE: protein     ( x i ) SEQUENCE DESCRIPTION: SEQ ID NO:6:

```
Glu  Lys  Pro  Leu  His  Ala  Leu  Leu  His  Gly  Arg  Gly  Val  Cys  Leu  Asn
 1                       5                       10                       15

Glu  Lys  Ser  Tyr  Arg  Glu  Gln  Val  Lys  Ile  Glu  Arg  Asp  Ser  Arg  Glu
                20                       25                       30

His  Glu  Glu  Pro  Thr  Thr  Ser  Glu  Met  Ala  Glu  Glu  Thr  Tyr  Ser  Pro
          35                       40                       45

Lys  Ile  Phe  Arg  Pro  Lys  His  Thr  Arg  Ile  Ser  Glu  Leu  Lys  Ala  Glu
     50                       55                       60

Ala  Val  Lys  Lys  Asp  Arg  Arg  Lys  Lys  Leu  Thr  Gln  Ser  Lys  Phe  Val
 65                       70                       75                       80

Gly  Gly  Ala  Glu  Asn  Thr  Ala  His  Pro  Arg  Ile  Ile  Ser  Glu  Pro  Glu
                85                       90                       95

Met  Arg  Gln  Glu  Ser  Glu  Gln  Gly  Pro  Cys  Arg  Arg  His  Met  Glu  Ala
               100                      105                      110

Ser  Leu  Gln  Glu  Leu  Lys  Ala  Ser  Pro  Arg  Met  Val  Pro  Arg  Ala  Val
          115                      120                      125

Tyr  Leu  Pro  Asn  Cys  Asp  Arg  Lys  Gly  Phe  Tyr  Lys  Arg  Lys  Gln  Cys
     130                      135                      140

Lys  Pro  Ser  Arg  Gly  Arg  Lys  Arg  Gly  Ile  Cys  Trp  Cys  Val  Asp  Lys
145                      150                      155                      160

Tyr  Gly  Met  Lys  Leu  Pro  Gly  Met  Glu  Tyr  Val  Asp  Gly  Asp  Phe  Gln
               165                      170                      175

Cys  His  Thr  Phe  Asp  Ser  Ser  Asn  Val  Glu
                180                      185
```

( 2 ) INFORMATION FOR SEQ ID NO:7:

( i ) SEQUENCE CHARACTERISTICS:
        ( A ) LENGTH: 1023 base pairs
        ( B ) TYPE: nucleic acid
        ( C ) STRANDEDNESS: double
        ( D ) TOPOLOGY: linear     ( i i ) MOLECULE TYPE: cDNA     ( i i i ) HYPOTHETICAL: NO     ( i x ) FEATURE:
        ( A ) NAME/KEY: CDS
        ( B ) LOCATION: 57..875

( x i ) SEQUENCE DESCRIPTION: SEQ ID NO:7:

```
CCCTGCACTC  TCGCTCTCCT  GCCCCACCCC  GAGGTAAAGG  GGGCGACTAA  GAGAAG                    56

ATG  GTG  TTG  CTC  ACC  GCG  GTC  CTC  CTG  CTG  CTG  GCC  GCC  TAT  GCG  GGG      104
Met  Val  Leu  Leu  Thr  Ala  Val  Leu  Leu  Leu  Leu  Ala  Ala  Tyr  Ala  Gly
 1                  5                        10                       15

CCG  GCC  CAG  AGC  CTG  GGC  TCC  TTC  GTG  CAC  TGC  GAG  CCC  TGC  GAC  GAG      152
Pro  Ala  Gln  Ser  Leu  Gly  Ser  Phe  Val  His  Cys  Glu  Pro  Cys  Asp  Glu
               20                        25                       30

AAA  GCC  CTC  TCC  ATG  TGC  CCC  CCC  AGC  CCC  CTG  GGC  TGC  GAG  CTG  GTC      200
Lys  Ala  Leu  Ser  Met  Cys  Pro  Pro  Ser  Pro  Leu  Gly  Cys  Glu  Leu  Val
          35                        40                       45

AAG  GAG  CCG  GGC  TGC  GGC  TGC  TGC  ATG  ACC  TGC  GCC  CTG  GCC  GAG  GGG      248
Lys  Glu  Pro  Gly  Cys  Gly  Cys  Cys  Met  Thr  Cys  Ala  Leu  Ala  Glu  Gly
     50                        55                       60

CAG  TCG  TGC  GGC  GTC  TAC  ACC  GAG  CGC  TGC  GCC  CAG  GGG  CTG  CGC  TGC      296
Gln  Ser  Cys  Gly  Val  Tyr  Thr  Glu  Arg  Cys  Ala  Gln  Gly  Leu  Arg  Cys
 65                 70                       75                            80

CTC  CCC  CGG  CAG  GAC  GAG  GAG  AAG  CCG  CTG  CAC  GCC  CTG  CTG  CAC  GGC      344
Leu  Pro  Arg  Gln  Asp  Glu  Glu  Lys  Pro  Leu  His  Ala  Leu  Leu  His  Gly
                    85                       90                       95

CGC  GGG  GTT  TGC  CTC  AAC  GAA  AAG  AGC  TAC  CGC  GAG  CAA  GTC  AAG  ATC      392
Arg  Gly  Val  Cys  Leu  Asn  Glu  Lys  Ser  Tyr  Arg  Glu  Gln  Val  Lys  Ile
               100                       105                      110

GAG  AGA  GAC  TCC  CGT  GAG  CAC  GAG  GAG  CCC  ACC  ACC  TCT  GAG  ATG  GCC      440
Glu  Arg  Asp  Ser  Arg  Glu  His  Glu  Glu  Pro  Thr  Thr  Ser  Glu  Met  Ala
          115                       120                      125

GAG  GAG  ACC  TAC  TCC  CCC  AAG  ATC  TTC  CGG  CCC  AAA  CAC  ACC  CGC  ATC      488
Glu  Glu  Thr  Tyr  Ser  Pro  Lys  Ile  Phe  Arg  Pro  Lys  His  Thr  Arg  Ile
     130                      135                      140

TCC  GAG  CTG  AAG  GCT  GAA  GCA  GTG  AAG  AAG  GAC  CGA  AGA  AAG  AAG  CTG      536
Ser  Glu  Leu  Lys  Ala  Glu  Ala  Val  Lys  Lys  Asp  Arg  Arg  Lys  Lys  Leu
145                      150                      155                      160

ACC  CAG  TCC  AAG  TTT  GTC  GGG  GGA  GCC  GAG  AAC  ACT  GCC  CAC  CCC  CGG      584
Thr  Gln  Ser  Lys  Phe  Val  Gly  Gly  Ala  Glu  Asn  Thr  Ala  His  Pro  Arg
                    165                      170                      175

ATC  ATC  TCT  GCA  CCT  GAG  ATG  AGA  CAG  GAG  TCT  GAG  CAG  GGC  CCC  TGC      632
Ile  Ile  Ser  Ala  Pro  Glu  Met  Arg  Gln  Glu  Ser  Glu  Gln  Gly  Pro  Cys
               180                      185                      190

CGC  AGA  CAC  ATG  GAG  GCT  TCC  CTG  CAG  GAG  CTC  AAA  GCC  AGC  CCA  CGC      680
Arg  Arg  His  Met  Glu  Ala  Ser  Leu  Gln  Glu  Leu  Lys  Ala  Ser  Pro  Arg
          195                      200                      205

ATG  GTG  CCC  CGT  GCT  GTG  TAC  CTG  CCC  AAT  TGT  GAC  CGC  AAA  GGA  TTC      728
Met  Val  Pro  Arg  Ala  Val  Tyr  Leu  Pro  Asn  Cys  Asp  Arg  Lys  Gly  Phe
     210                      215                      220

TAC  AAG  AGA  AAG  CAG  TGC  AAA  CCT  TCC  CGT  GGC  CGC  AAG  CGT  GGC  ATC      776
Tyr  Lys  Arg  Lys  Gln  Cys  Lys  Pro  Ser  Arg  Gly  Arg  Lys  Arg  Gly  Ile
```

```
225                     230                     235                     240
TGC  TGG  TGC  GTG  GAC  AAG  TAC  GGG  ATG  AAG  CTG  CCA  GGC  ATG  GAG  TAC     824
Cys  Trp  Cys  Val  Asp  Lys  Tyr  Gly  Met  Lys  Leu  Pro  Gly  Met  Glu  Tyr
               245                     250                     255

GTT  GAC  GGG  GAC  TTT  CAG  TGC  CAC  ACC  TTC  GAC  AGC  AGC  AAC  GTT  GAG     872
Val  Asp  Gly  Asp  Phe  Gln  Cys  His  Thr  Phe  Asp  Ser  Ser  Asn  Val  Glu
               260                     265                     270

TGATGCGTCC  CCCCCCAACC  TTTCCCTCAC  CCCCTCCCAC  CCCCAGCCCC  GACTCCAGCC              932

AGCGCCTCCC  TCCACCCCAG  GACGCCACTC  ATTTCATCTC  ATTTAAGGGA  AAAATATATA              992

TCTATCTATT  TGAAAAAAAA  AAAAAAAACC  C                                              1023
```

( 2 ) INFORMATION FOR SEQ ID NO:8:

( i ) SEQUENCE CHARACTERISTICS:
        ( A ) LENGTH: 272 amino acids
        ( B ) TYPE: amino acid
        ( D ) TOPOLOGY: linear     ( i i ) MOLECULE TYPE: protein     ( x i ) SEQUENCE DESCRIPTION: SEQ ID NO:8:

```
Met  Val  Leu  Leu  Thr  Ala  Val  Leu  Leu  Leu  Ala  Ala  Tyr  Ala  Gly
 1              5                        10                      15

Pro  Ala  Gln  Ser  Leu  Gly  Ser  Phe  Val  His  Cys  Glu  Pro  Cys  Asp  Glu
               20                       25                      30

Lys  Ala  Leu  Ser  Met  Cys  Pro  Pro  Ser  Pro  Leu  Gly  Cys  Glu  Leu  Val
               35                       40                      45

Lys  Glu  Pro  Gly  Cys  Gly  Cys  Cys  Met  Thr  Cys  Ala  Leu  Ala  Glu  Gly
          50                      55                       60

Gln  Ser  Cys  Gly  Val  Tyr  Thr  Glu  Arg  Cys  Ala  Gln  Gly  Leu  Arg  Cys
 65                            70                       75                     80

Leu  Pro  Arg  Gln  Asp  Glu  Glu  Lys  Pro  Leu  His  Ala  Leu  Leu  His  Gly
               85                       90                      95

Arg  Gly  Val  Cys  Leu  Asn  Glu  Lys  Ser  Tyr  Arg  Glu  Gln  Val  Lys  Ile
               100                      105                     110

Glu  Arg  Asp  Ser  Arg  Glu  His  Glu  Glu  Pro  Thr  Thr  Ser  Glu  Met  Ala
               115                      120                     125

Glu  Glu  Thr  Tyr  Ser  Pro  Lys  Ile  Phe  Arg  Pro  Lys  His  Thr  Arg  Ile
     130                      135                      140

Ser  Glu  Leu  Lys  Ala  Glu  Ala  Val  Lys  Lys  Asp  Arg  Arg  Lys  Lys  Leu
145                      150                      155                     160

Thr  Gln  Ser  Lys  Phe  Val  Gly  Gly  Ala  Glu  Asn  Thr  Ala  His  Pro  Arg
               165                      170                     175

Ile  Ile  Ser  Ala  Pro  Glu  Met  Arg  Gln  Glu  Ser  Glu  Gln  Gly  Pro  Cys
               180                      185                     190

Arg  Arg  His  Met  Glu  Ala  Ser  Leu  Gln  Glu  Leu  Lys  Ala  Ser  Pro  Arg
          195                      200                      205

Met  Val  Pro  Arg  Ala  Val  Tyr  Leu  Pro  Asn  Cys  Asp  Arg  Lys  Gly  Phe
          210                      215                      220

Tyr  Lys  Arg  Lys  Gln  Cys  Lys  Pro  Ser  Arg  Gly  Arg  Lys  Arg  Gly  Ile
225                      230                      235                     240

Cys  Trp  Cys  Val  Asp  Lys  Tyr  Gly  Met  Lys  Leu  Pro  Gly  Met  Glu  Tyr
               245                      250                     255

Val  Asp  Gly  Asp  Phe  Gln  Cys  His  Thr  Phe  Asp  Ser  Ser  Asn  Val  Glu
               260                      265                     270
```

(2) INFORMATION FOR SEQ ID NO:9:

(i) SEQUENCE CHARACTERISTICS:
        (A) LENGTH: 8 amino acids
        (B) TYPE: amino acid
        (D) TOPOLOGY: linear     (ii) MOLECULE TYPE: peptide     (xi) SEQUENCE DESCRIPTION: SEQ ID NO:9:

Asp Tyr Lys Asp Asp Asp Asp Lys
1             5